United States Patent [19]

Bourgeois et al.

[11] Patent Number: 4,931,185
[45] Date of Patent: Jun. 5, 1990

[54] METHOD AND APPARATUS INTENDED FOR THE FILTRATION ON A MEMBRANE OF A PRODUCT SUCH AS MILK

[75] Inventors: Claude Bourgeois; Jean-Yves Colin, both of Quimper, France

[73] Assignee: A.D.R.I.A., Quimper, France

[21] Appl. No.: 26,759

[22] PCT Filed: Jun. 9, 1986

[86] PCT No.: PCT/FR86/00198
§ 371 Date: Mar. 31, 1987
§ 102(e) Date: Mar. 31, 1987

[87] PCT Pub. No.: WO86/07279
PCT Pub. Date: Dec. 18, 1986

[30] Foreign Application Priority Data

Jun. 11, 1985 [FR] France .............................. 85 089992

[51] Int. Cl.⁵ .............................................. B01D 13/00
[52] U.S. Cl. ..................................... 210/636; 210/232; 210/651
[58] Field of Search ............... 210/636, 232, 409, 411, 210/651, 650

[56] References Cited

U.S. PATENT DOCUMENTS

| | | | |
|---|---|---|---|
| 2,763,308 | 9/1956 | Samler | 146/174 |
| 2,904,857 | 9/1959 | Goetz | 21/82 |
| 3,448,011 | 6/1969 | Russomanno | 195/139 |
| 4,094,784 | 6/1978 | Hirano | 210/68 |
| 4,579,662 | 4/1986 | Jonsson | 210/636 |
| 4,738,782 | 4/1988 | Yamauchi et al. | 210/650 |

FOREIGN PATENT DOCUMENTS 1949059 4/1971 Fed. Rep. of Germany.

OTHER PUBLICATIONS

Membranfiltration in der kosmetischen Industrie, Kosmetik und Aerosole, vol 99, #13, Jun. 14, 1973.

*Primary Examiner*—Frank Spear
*Attorney, Agent, or Firm*—Roland Plottel

[57] ABSTRACT

Method and apparatus intended for the filtration on a membrane of a product such as milk with a view to analysing filtration products recovered on the membrane. The method comprises the filtration under pressure and the rinsing by means of different elements without any risk of deteriorating or polluting the active filter. The apparatus which comprises two active elements (100) and (200) is particularly characterized by the combination of means for supplying a pressurized tank (3) with different liquids, and a filter holder (10) which is wedged by means of two inclined planes (P1) and (P2) driven by means of a jack (14) so that they are sealingly superposed. The invention applies particularly to the analysis of milk with a view to numbering the Clostridium Tyrobutyricum, or any other microorganism.

6 Claims, 2 Drawing Sheets

METHOD AND APPARATUS INTENDED FOR THE FILTRATION ON A MEMBRANE OF A PRODUCT SUCH AS MILK

The present invention relates to a device for filtering a liquid and collecting on a membrane elements in suspension in this liquid for analysis thereof.

An example of application of this method and this apparatus, in accordance with the invention, relates more particularly to the analysis of milk.

For example, when it is desired to count in milk spores of Clostridium Tyrobutyricum which adversely affect the quality of cheeses particularly of the Emmental type, a method is required responding to high requirements of sensitivity and speed.

A method perfected by the applicant and which has already been published consists in concentrating the spores by filtering the milk under pressure through a filtering membrane, and in counting the colonies obtained on this filtering membrane applied on the selective gelose medium, after sufficient incubation time. In its principle this method is not original, what is original are the precise conditions for such filtration allowing volumes of milk to be filtered very much greater than those which can be filtered using the usual methods.

A difficulty arises in positioning and recovering the filter, as well as in the filtration procedure which must comply with very strict criteria of filtered volume, convenience in use and absence of parasite contaminations which are not satisfied by existing methods.

Analytic filtration is usually carried out using devices operating by suction, guaranteeing the absence of contamination of the filter, and easy use adapted to the high rates required by the analysis.

In the case of liquids which are not readily filterable, such as milk, it is advantageous to increase the filtered volume to work under pressure, but the pressurized filtration apparatus available commercially, intended for the preparatory sterilization of the liquids, are not adapted to the repeated high rate use required by the analysis, and do not readily ensure the absence of parasite contamination of the filter.

The purpose of the present invention is precisely to describe a method and equipment for carrying out the analytic filtration operations under pressure under better conditions of convenience of use and recovery of the constituents to be analyzed.

The invention relates to the filtration of milk such as described above by way of example, but may also apply to the filtration of other liquids.

It relates more precisely to a method for filtering a product under pressure, on a filter or porous membrane, for recovering microorganisms on said filter, characterized in that it includes three essential cycles carried out using the same apparatus, namely:

Cycle A: Filling of a reservoir with a liquid to be analyzed and pressurization thereof, that the liquid introduced into the reservoir transits under pressure through the filter before being discharged.

Cycle B: Rinsing of the filter by introducing a rinsing product into the reservoir, the filter being still in position.

Cycle C: Recovery of the filter and positioning of a substitution filter.

Cycle D: Rinsing of the reservoir by introducing a disinfectant agent therein.

The invention also relates to an apparatus for implementing the method, characterized in that it comprises a filter holder (membrane) whose positioning in particularly easy.

The invention will be better understood from the description of the apparatus and the operation thereof which follows, and from the accompanying Figures in which.

For the sake of clarity, the same elements bear the same references in all the Figures.

Figure 1:
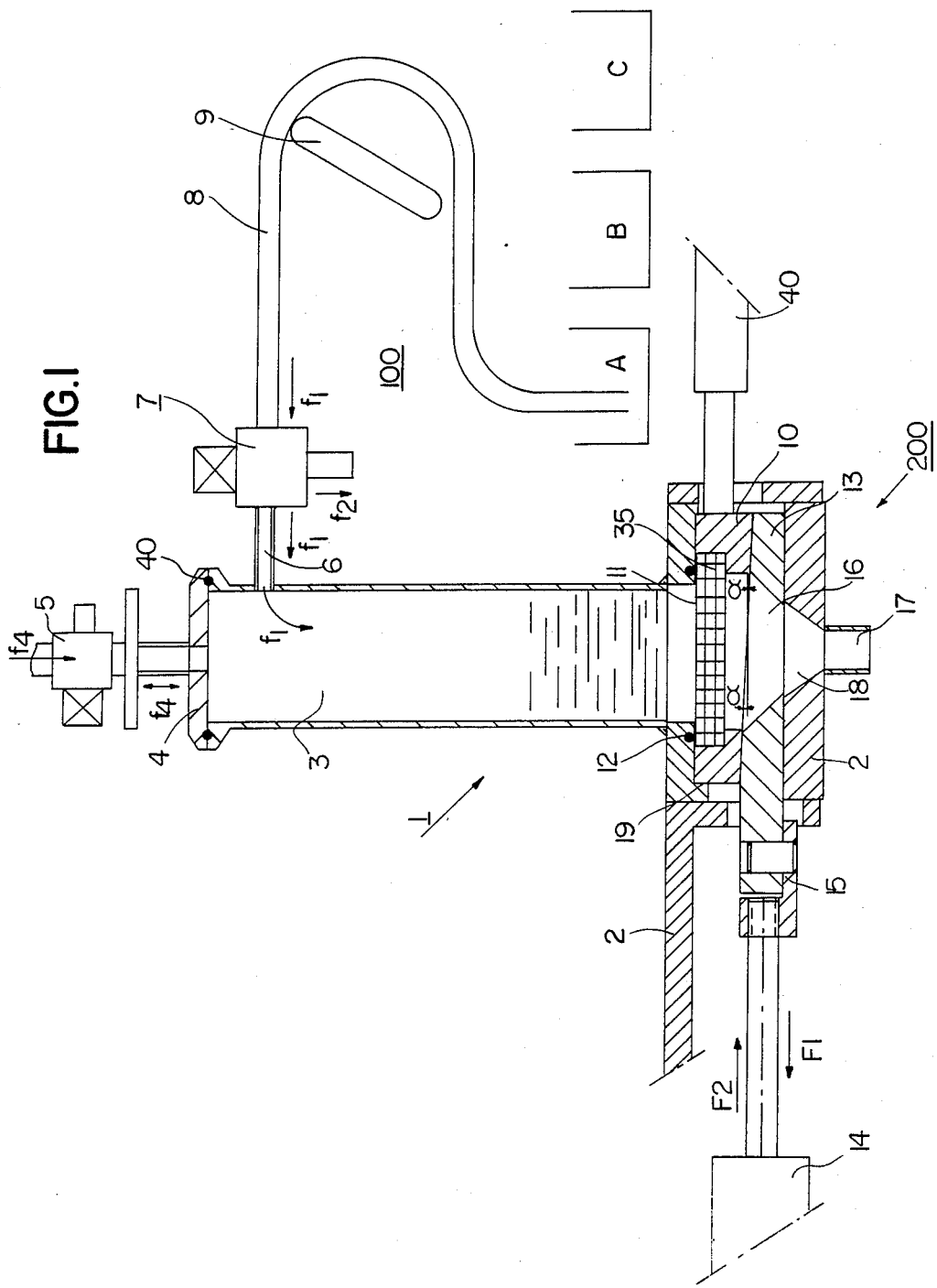
FIG. 1 shows the assembly of the filtration device, the system for locking the filter being in the operational position.
Figure 3:
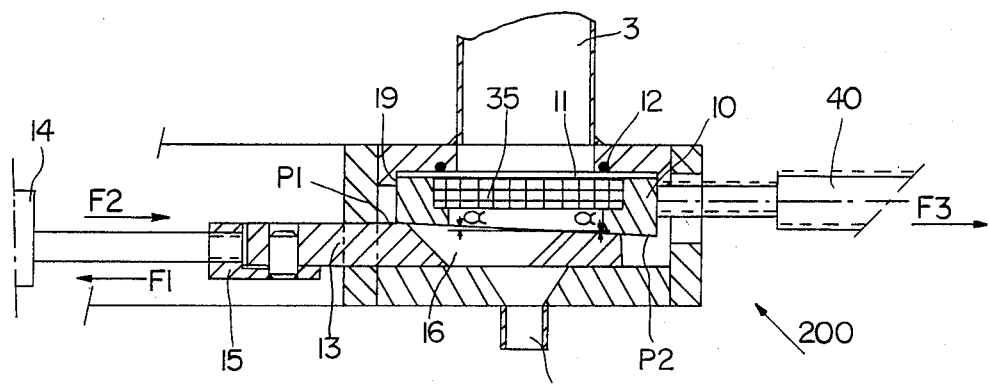
FIG. 3 shows this system for locking the filter and filter holder, in the released position.
Figure 2:
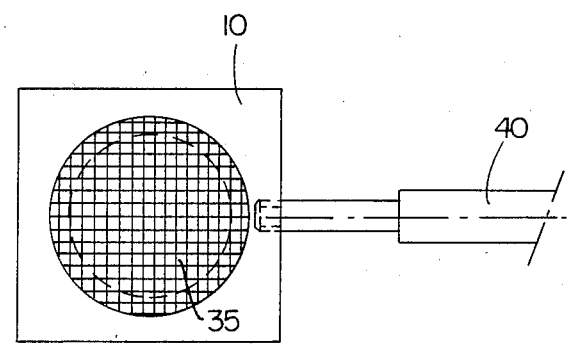
FIG. 2 is a top view of the filter holder.

As shown in FIGS. 1 to 3, this apparatus is characterized in that it is formed of a case 2, shown schematically, which receives two active assemblies.

The first active assembly 100, disposed vertically on the upper part of the apparatus, includes a cylinder 3 serving as reservoir for the product to be filtered, with associated supply and pneumatic systems.

At the top of this reservoir 3 is located a sealed cover 4 fixed via an O seal 40, in which a pneumatic system 5 is fitted. A supply tube 6, associated with an electromagnetic assembly 7, opens into the reservoir cylinder 3, along a generatrix, and, at the top thereof. It allows the liquid to be analyzed as well as different addition and rinsing liquids to be introduced into reservoir 3, in accordance with a programmed cycle adapted to the filtering to be effected, without raising the sealed cover 4 from the reservoir, through a flexible pipe 8 and a pump 9, (a vane pump for example), these liquids being taken from containers A, B or C depending on the composition of the liquids and on the needs and order of introduction thereof.

The second active assembly 200, called drawer in the rest of the description, is placed in the lower part of the apparatus, under the reservoir cylinder 3.

It is formed of a removable filter holder 10, provided with a handle 40, which receives a filter 11 which is nothing but a porous membrane on which the filtration products will be deposited and collected for analysis.

Filter 11, on its filter holder 10, is held sealingly in contact with the liquid to be filtered by means of an O seal 12 and, according to one of the characteristics of the invention, by means of a wedge system 13 which may be retracted under the action of an actuating cylinder 14 cooperating with a connection system 15 having several degrees of freedom, preventing any untimely locking during operation. In the metal plate forming wedge 13 a passage 16 is provided for discharging the filtered liquid.

The correct wedging and sealing of the system, apart from the O seal, is obtained by the cooperation of two inclined planes P1 and P2, of angle ($\alpha$), respectively of wedge 13 and of filter holder 10. In the example chosen, the angle ($\alpha$) is of the order of 2°.

By moving wedge 13 back under the action of the actuator 14, in the direction of arrow F1, the vertical pressure exerted on the filter holder 10 and its filter 11 is removed, these latter then being able to be recovered with the elements to be analyzed.

The liquid is discharged during the filtering operation, through orifice 17, by flowing through the bottom of the body 2 of the apparatus through a conical orifice 18 provided for this purpose.

In FIG. 13, the existence and position of a grid 35 has been shown placed in the cavity of the filter holder 10, on which the filter 11 bears so as to hold it flat, without preventing the liquid from flowing through the device.

A priviledged application of the invention, using a device in accordance with the invention such as described above, will now be described.

It is a question of collecting micro-organisms, for example Clostridium Tyrobutyricum, in suspension in milk for the purpose of analyzing them. The cover 4 associated with its pneumatic system 5 is assumed in position, as well as the supply system 100 ready to operate, the inside of the device being clean and sterile.

The filter holder 10 is withdrawn from its drawer 200 and ready to receive a circular filter 11. Wedge 13 is in the retracted position. As shown in FIG. 3, the filter holder 10 and its filter 11 are fitted into the drawer up to its abutment point 19. The filter holder and its filter 11 may then be refitted and locked, under the action of the actuating cylinder 14 pushing wedge 13 in the direction of arrow F2.

The required and sufficient amount of milk, coming from container A for example, is then introduced into the reservoir 3 by means of the pump 9 and the electromagnetic valve system 7 positioned in the passing direction shown by arrow F1.

Cylinder 3 is then pressurized with air through the electromagnetic valve 5, positioned in the passing direction shown by arrow F4 (in the example chosen, the pressure is 3 bars). Under the effect of the pressure, filtration begins through filter 11, the liquid being discharged through orifice 17 and the micro-organisms being deposited on filter 11.

After total filtration of the amount of milk introduced into reservoir 3, the air pressure is released by operating the electromagnetic valve 5. A rinsing operation with water is then carried out, without the need of opening reservoir 3.

This water, which may be in container B, is then introduced into reservoir 3 after moving pipe A from A to B, then is discharged through orifice 17, in accordance with the same procedure as described for introducing and discharging the milk.

After this rinsing operation, the microorganisms deposited on filter 11 may be recovered. In accordance with the invention and according to an important feature of the invention related more particularly to the architecture of the filter holder described above, this delicate operation, which must neither tear away nor pollute the filter 11 and its deposit to be analyzed, is carried out in the shortest time and under optimum conditions.

For recovering the filter under the desired conditions, it is in fact sufficient to retract wedge 13, under the action of the actuating cylinder 14 in the direction of arrow F1 for releasing and causing the filter holder 10 and its filter 11 to move down sufficiently so that by pulling the filter holder 10 by means of handle 40 in the direction of arrow 3 and possibly by pivoting it, the filter holder may be removed without any contact or rubbing of the filter.

After repositioning of the filter holder without filter or with a substitution filter, cleaning may be carried out following the above described procedure, by switching the pipes to container C by a manual or automatic and programmed means.

The whole of the filtering and cleaning operation may then be carried out in a succession of steps which may be grouped together in five main cycles and described below.

Cycle A

1. Positioning of the filter 11 on the filter holder 10.
2. Positioning of the filter holder 10 in the drawer 200 (tube 8 is switched to container A containing the milk to be filtered).
3. Opening of the electromagnetic valve 7 for introducing the milk into the reservoir 3 in the direction of arrow F1, under the action of the pump 9 (electromagnetic valve 5 is closed).
4. Closure of the electromagnetic valve 7 after introduction of the milk into the reservoir 3 in a sufficient and required amount (previously fixed quantity control by volume).
5. Opening of the electromagnetic valve 5, pressurization to 3 bars (for example) in the direction of arrow F4, passage of the milk through the filter under the effect of the air pressure, and discharge through orifice 17 of the filtered liquid.
6. Closure of the electromagnetic valve 5.

Cycle B: Rinsing with water

7. Switching of tube 8 from container A to container B containing the water.
8. Opening of the electromagnetic valve 7 and starting up of pump 9.
9. Intake of water and filling of reservoir 3 therewith.
10. Closure of the electromagnetic valve 7.
11. Opening of the electromagnetic valve 5 bringing the pressurized air in the direction of arrow F4. Passage of water through the filter under the effect of the air pressure (the micro-organism deposited are not entrained). Discharge of the water through orifice 17.
12. Closure of the electromagnetic valve 5.

Cycle C: Recovery of the deposits to be analysed (at this stage, the electromagnetic valves 5 and 7 are closed)

13. Opening of drawer 200 (as was explained in the description of the second active assembly), and removal of the filter holder 10 and its filter 11.
14. Recovery of the filter 11 and its deposit of micro-organisms to be analyzed.

Cycle D: Specific cleaning of the device

15. Fitting of a filter on the filter holder 10 (this substitution filter will be lost).
16. Fitting of the filter holder 10 into the drawer 200.
17. Switching of pipe 8 to container C containing a specific rinsing or asepticizing solution.
18. Cycle B, step (8), may then be repeated until recovery of the substitution filter which will be destroyed.

CYCLE E: Rinsing with milk

This cycle consists in putting the whole of the device and its piping in the atmosphere of the milk or liquid to be filtered.

It is then sufficient to switch pipe A to recipient A containing the milk to be analysed, and to carry out a cycle A from sequence 2, after placing a substitution filter on the filter holder 10 or not.

After replacing an active filter 11, the complete cycles A to C may then be carried out for recovering the elements to be analyzed.

All these cycles may be carried out as many times as desired without the operator being obliged to carry out fastidious, time consuming dismantling operations often unreliable from the cleaning point of view.

The application of such a device are numerous and are to be found in the case of analyzing milk (application described by way of example), but also in the technique of manufacturing a large number of products such as beer for example.

We claim:

1. A method for effecting the filtration of a product, on a filter or a filtering membrane (11), for recovering micro-organisms on said filter (11) for analysis of said recovered micro-organisms, characterized in that it includes the following essential cycles performed by means of the same apparatus, namely:

Cycle A: Filling of a reservoir (3) and pressurization thereof, so that the liquid introduced into the reservoir (3) transmits under pressure through the filter (11) before being discharged.

Cycle B: Rinsing of the filter (11) by introduction of a rinsing product into the reservoir, the filter (11) being still in position.

Cycle C: Recovering of the filter (11) and positioning of a substitution filter.

Cycle D: Rinsing of the reservoir (3) by introducing a disinfectant agent therein.

2. Method according to claim 1, characterized in that, is cycle (B), rinsing is effected using the liquid to be studied, before replacement of the substitution filter by a new filter (11).

3. Apparatus for implementing the method claim 1, characterized in that it comprises a case (2) on which is vertically disposed an active assembly (100) including a reservoir (3), this active assembly placing this reservoir (3) successively in communication with containers (A), (B), and (C), the first one containing the product to be filtered, the second a rinsing product, and the third a disinfection product; all these elements cooperating with a drawer (200) comprising a removable filter holder (10) receiving a filter (11).

4. Apparatus according to claim 3, characterized in that the filter (11), positioned on its filter holder (10) is held sealingly in contact with the contents of the reservoir (3) by means of a wedge system (13).

5. Apparatus according to claim 4, characterized in that this wedge system (13) may be retracted under the action of an actuating cylinder (14).

6. Apparatus according to claim 4, characterized in that wedging is obtained by the cooperation of two inclined planes (P1) and (P2) forming an angle ($\alpha$) therebetween.

* * * * *